US00PP19698P2

(12) United States Plant Patent
Fisher et al.

(10) Patent No.: US PP19,698 P2
(45) Date of Patent: Feb. 10, 2009

(54) ***MANDEVILLA* PLANT NAMED 'DIP 79'**

(50) Latin Name: *Mandevilla splendens*
Varietal Denomination: DIP 79

(75) Inventors: Wes Fisher, Sebring, FL (US); Dick Kearley, Hawthorne, FL (US)

(73) Assignee: Robrick Nursery, Inc., Hawthorne, FL (US)

( * ) Notice: Subject to any disclaimer, the term of this patent is extended or adjusted under 35 U.S.C. 154(b) by 0 days.

(21) Appl. No.: 12/069,041

(22) Filed: Feb. 6, 2008

(51) Int. Cl.
*A01H 5/00* (2006.01)

(52) U.S. Cl. ..... Plt./232
(58) Field of Classification Search ..... Plt./232
See application file for complete search history.

*Primary Examiner*—Annette H Para
*Assistant Examiner*—S. B. McCormick Ewoldt
(74) *Attorney, Agent, or Firm*—C. A. Whealy

(57) ABSTRACT

A new and distinct cultivar of *Mandevilla* plant named 'DIP 79', characterized by its upright and vining plant habit; vibrant red-colored flowers; and year-round flowering period.

2 Drawing Sheets

Botanical designation: *Mandevilla splendens.*
Cultivar denomination: 'DIP 79'.

BACKGROUND OF THE INVENTION

The present invention relates to a new and distinct cultivar of *Mandevilla,* botanically known as *Mandevilla splendens* and hereinafter referred to by the name 'DIP 79'.

The new *Mandevilla* is a product of a planned breeding program conducted by the Inventors in Sebring, Fla. The objective of the breeding program is to create new *Mandevilla* cultivars with dense foliage and red-colored flowers.

The new *Mandevilla* originated from an open-pollination during May, 2003 in Sebring, Fla. of the *Mandevilla splendens* cultivar Red Riding Hood, not patented, as the female, or seed parent with an unknown selection of *Mandevilla splendens* as the male, or pollen, parent. The cultivar DIP 79 was discovered and selected by the Inventors as a flowering plant from within the progeny of the stated open-pollination in a controlled environment in Sebring, Fla. May, 2004.

Asexual reproduction of the new cultivar by cuttings in Sebring, Fla. since March, 2005, has shown that the unique features of this new *Mandevilla* are stable and reproduced true to type in successive generations.

SUMMARY OF THE INVENTION

Plants of the cultivar DIP 79 have not been observed under all possible environmental conditions. The phenotype may vary somewhat with variations in environment such as temperature and light intensity without, however, any variance in genotype.

The following traits have been repeatedly observed and are determined to be the unique characteristics of 'DIP 79'. These characteristics in combination distinguish 'DIP 79' as a new and distinct cultivar:

1. Upright and vining plant habit.
2. Vibrant red-colored flowers.
3. Year-round flowering period.

Plants of the new *Mandevilla* differ primarily from plants of the female parent, the cultivar Red Riding Hood, in the following characteristics:

1. Plants of the new *Mandevilla* are larger and more vigorous and vining than plants of the cultivar Red Riding Hood.
2. Plants of the new *Mandevilla* are more freely branching than plants of the cultivar Red Riding Hood.
3. Plants of the new *Mandevilla* are more freely flowering than plants of the cultivar Red Riding Hood.
4. Plants of the new *Mandevilla* have darker red-colored flowers than plants of the cultivar Red Riding Hood.

Plants of the new *Mandevilla* can also be compared to plants of the *Mandevilla* cultivar Sunmandecrim, disclosed in U.S. Plant Pat. No. 15,539. In side-by-side comparisons conducted in Sebring, Fla., plants of the new *Mandevilla* differed from plants of the cultivar Sunmandecrim in the following characteristics:

1. Plants of the new *Mandevilla* were more strongly vining than plants of the cultivar Sunmandecrim.
2. Plants of the new *Mandevilla* were larger and more vigorous than plants of the cultivar Sunmandecrim.
3. Plants of the new *Mandevilla* had larger and lighter green-colored leaves than plants of the cultivar Sunmandecrim.
4. Plants of the new *Mandevilla* flowered earlier and more freely than plants of the cultivar Sunmandecrim.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

The photograph on the first sheet comprises a side perspective view of a typical flowering plant of 'DIP 79' grown in a container.

The photograph on the second sheet is a close-up view of typical plants of 'DIP 79', 'Red Riding Hood' and 'Sunmandecrim' (left to right).

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the autumn and winter in a polyethylene-covered greenhouse in Sebring, Fla. for about 13 weeks in 25-cm containers. Plants were pinched one time about two weeks after planting. During the production of the plants, day temperatures ranged from 21° C. to 38° C. and night temperatures averaged 24° C.

Botanical classification: *Mandevilla splendens* cultivar DIP 79.

Parentage:

*Female, or seed, parent.*—*Mandevilla splendens* cultivar Red Riding Hood, not patented.

*Male, or pollen, parent.*—Unknown selection of *Mandevilla splendens,* not patented.

Propagation:

*Type.*—By tip cuttings.

*Time to initiate roots.*—About three weeks at 24° C. to 29° C.

*Time to produce a rooted young plant.*—About six to seven weeks at 24° C. to 29° C.

*Root description.*—Fibrous, medium in thickness; 162D in color.

*Rooting habit.*—Moderate branching; moderately dense.

Plant description:

*Form.*—Perennial. Upright and strongly vining plant habit. Vigorous growth habit.

*Plant height.*—About 120 cm.

*Plant diameter* (*spread*).—About 25 cm.

*Lateral branch description.*—Length: About 14 cm. Diameter: About 2 mm. Internode length: About 5 cm. Strength: Flexible, strong. Texture: Smooth, glabrous. Color: 144A.

Foliage description:

*Arrangement.*—Opposite, simple.

*Length.*—About 6.7 cm.

*Width.*—About 3.9 cm.

*Shaped.*—Obovate.

*Apex.*—Cuspidate.

*Base.*—Obtuse.

*Margin.*—Entire.

*Texture, upper and lower surfaces.*—Smooth, glabrous.

*Venation pattern.*—Pinnate.

*Color.*—Developing foliage, upper surface: 137A. Developing foliage, lower surface: 137C. Fully expanded foliage, upper surface: 139A; venation, 146C. Fully expanded foliage, lower surface: 146B; venation, 145D.

*Petiole length.*—About 1.5 cm.

*Petiole diameter.*—About 1.5 mm.

*Petiole texture, upper and lower surfaces.*—Smooth, glabrous.

*Petiole color, upper surface.*—Close to 139A.

*Petiole color, lower surface.*—Close to 146B.

Flower description:

*Flower type and habit.*—Single salverform flowers; flowers racemose; flowers face mostly outwardly to slightly upright. Flowers not persistent. Freely flowering habit, about five flowers per inflorescence.

*Natural flowering season.*—Plants of the new *Mandevilla* flower year-round in Florida.

*Flower longevity on the plant.*—About three to five days. Flowers not persistent.

*Fragrance.*—None detected.

*Flowers.*—Appearance: Flared trumpet, corolla fused, five-parted; petals imbricate; flowers roughly star-shaped. Diameter: About 7 cm. Depth (length): About 5 cm. Throat diameter: About 1.5 cm. Tube length: About 4.1 cm.

*Flower buds.*—Length: About 4 cm. Diameter: About 1 cm. Shape: Cylindrical, pointed. Color: 46A.

*Corolla.*—Arrangement/appearance: Single whorl of five petals, fused into flared trumpet; petals imbricate. Petal length: About 2.5 cm. Petal width: About 2 cm. Petal shape: Spatulate. Petal apex: Cuspidate. Petal margin: Entire. Petal texture, upper and lower surfaces: Smooth, glabrous; velvety. Color: Petal, when opening and fully opened, upper surface: Close to 53A; color becoming closer to 53B with development. Petal, when opening and fully opened, lower surface: Close to 53B; color becoming closer to 53C with development.

*Sepals.*—Arrangement/appearance: Five per flower in a single whorl; fused. Length: About 7.5 mm. Width: About 1 mm. Shape: Lanceolate. Apex: Sharply acute. Margin: Entire. Texture, upper and lower surfaces: Smooth, glabrous. Color, upper and lower surfaces: 145D.

*Peduncles.*—Length: About 3 cm. Diameter: About 2.5 mm. Texture: Smooth, glabrous. Strength: Flexible, but strong. Color: 144B.

*Pedicels.*—Length: About 2 cm. Diameter: About 2 mm. Texture: Smooth, glabrous. Strength: Flexible, but strong. Color: 144B.

*Reproductive organs.*—Stamens: Quantity/arrangement: Typically five; filaments fused to corolla; anthers, connivent. Filament length: About 2 cm. Filament color: Close to 155D. Anther shape: Oblong elongated. Anther length: About 3 mm. Anther color: Close to 11A. Pollen amount: Scarce. Pollen color: Close to 11A. Pistils: Quantity: Typically one. Pistil length: About 2.5 cm. Stigma shape: Oblong to round. Stigma color: 11D. Style color: Close to 155D. Ovary color: 45A.

*Seed/fruit.*—Seed and fruit production has not been observed.

Disease/pest resistance: Plants of the new *Mandevilla* have been noted to be somewhat resistant to Fusarium. Plants of the new *Mandevilla* have not been noted to resistant to pests and other pathogens common to *Mandevilla.*

Temperature tolerance: Plants of the new *Mandevilla* have been observed to tolerate temperatures from about 0° C. to about 43° C.

It is claimed:

1. A new and distinct *Mandevilla* plant named 'DIP 79' as illustrated and described.

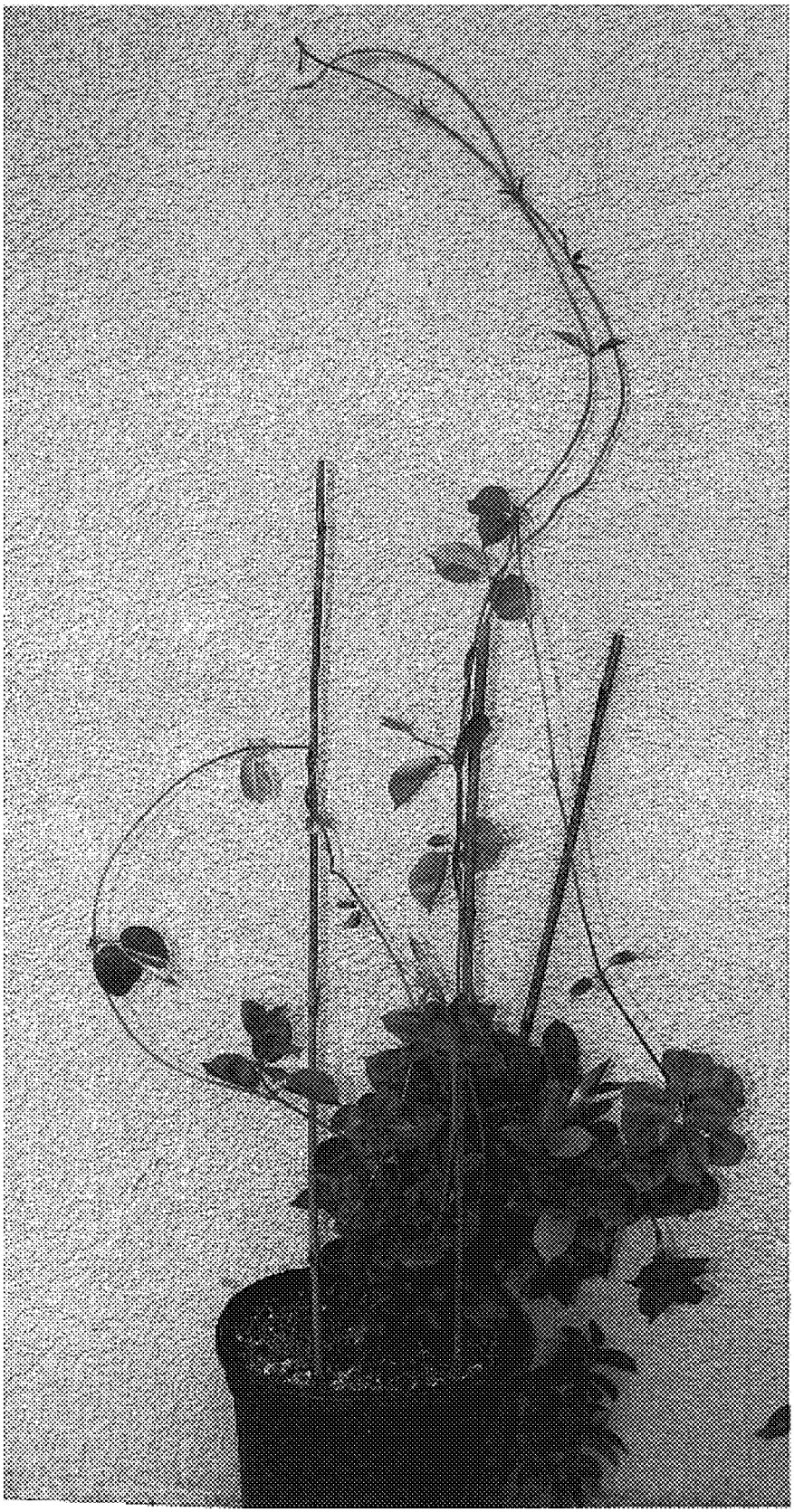

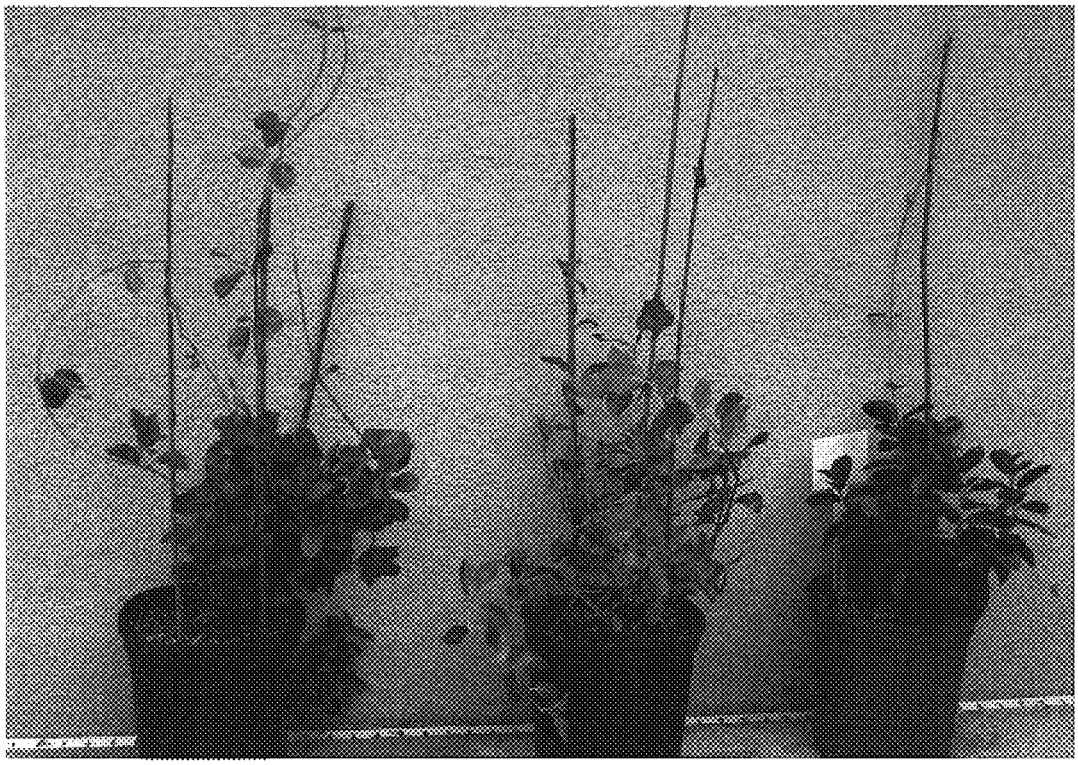

* * * * *